United States Patent
Brelidze et al.

(10) Patent No.: US 11,529,324 B2
(45) Date of Patent: Dec. 20, 2022

(54) USE OF KV11.1 CHANNEL INHIBITORS FOR TREATMENT OF PULMONARY HYPERTENSION

(71) Applicant: Georgetown University, Washington, DC (US)

(72) Inventors: Tinatin I. Brelidze, Washington, DC (US); Yuichiro J. Suzuki, Bethesda, MD (US); Nataliia Shults, Ashburn, VA (US); Vladyslava Rybka, Ashburn, VA (US)

(73) Assignee: GEORGETOWN UNIVERSITY, Washington, DC (US)

( * ) Notice: Subject to any disclaimer, the term of this patent is extended or adjusted under 35 U.S.C. 154(b) by 0 days.

(21) Appl. No.: 16/880,376

(22) Filed: May 21, 2020

(65) Prior Publication Data
US 2020/0383941 A1   Dec. 10, 2020

Related U.S. Application Data

(60) Provisional application No. 62/852,020, filed on May 23, 2019.

(51) Int. Cl.
   *A61K 31/18*   (2006.01)
   *A61K 9/00*    (2006.01)

(52) U.S. Cl.
   CPC ............ *A61K 31/18* (2013.01); *A61K 9/0019* (2013.01); *A61K 9/0053* (2013.01); *A61K 9/0073* (2013.01)

(58) Field of Classification Search
   CPC ................................ A61K 31/63; A61K 31/18
   See application file for complete search history.

(56) References Cited

PUBLICATIONS

Khadka et al. CAS: 163: 500625, 2015.*
Serafimovski et al. American Journal of Cardiology, 2008, 101(11): 1574-1579.*
Olsson et al. Int J Cardiol, 2013, 167(5): 2300-5.*
Hill et al. , Mol Pharmacol, 2014, 85(5):769-76.*
Akbarali et al., "Role of HERG-like K(+) currents in opossum esophageal circular smooth muscle", American Journal of Physiology, 1999, vol. 277, pp. C1284-C1290.
Arcangeli et al., "A novel inward-rectifying K+ current with a cell-cycle dependence governs the resting potential of mammalian neuroblastoma cells", Journal of Physiology, 1995, vol. 489, Part 2, pp. 455-471.
Austin et al., "The Genetics of Pulmonary Arterial Hypertension", Circ Res., 2014, vol. 115, No. 1, pp. 189-202.
Babcock et al., "hERG channel function: beyond long QT", Acta Pharmacologica Sinica, 2013, vol. 34, pp. 329-335.
Bartoszewski et al., "Ion channels of the lung and their role in disease pathogenesis", American Journal of Physiology Lung Cellular and Molecular Physiology, Nov. 1, 2017, vol. 313, No. 5, pp. L859-L872.
Bianchi et al., "herg encodes a K+ current highly conserved in tumors of different histogenesis: a selective advantage for cancer cells?", Cancer Research, Mar. 1998, vol. 58, No. 4, pp. 815-822.
Boucherat O, Chabot S, Antigny F, Perros F, Provencher S and Bonnet S. Potassium channels in pulmonary arterial hypertension. Eur Respir J. 2015;46:1167-77.
Cherubini A, Hofmann G, Pillozzi S, Guasti L, Crociani O, Cilia E, Di Stefano P, Degani S, Balzi M, Olivotto M, Wanke E, Becchetti A, Defilippi P, Wymore R and Arcangeli A. Human ether-a-go-go-related gene 1 channels are physically linked to beta1 integrins and modulate adhesion-dependent signaling. Mol Biol Cell. 2005;16:2972-83.
Colvin KL and Yeager ME. Animal Models of Pulmonary Hypertension: Matching Disease Mechanisms to Etiology of the Human Disease. J Pulm Respir Med. 2014;4.
Cordeiro S, Guseva D, Wulfsen I and Bauer CK. Expression pattern of Kv11 (Ether a-go-go-related gene; erg) K+ channels in the mouse retina. PLoS One. 2011;6:e29490.
Crociani O, Guasti L, Balzi M, Becchetti A, Wanke E, Olivotto M, Wymore RS and Arcangeli A. Cell cycle-dependent expression of HERG1 and HERG1B isoforms in tumor cells. J Biol Chem. 2003;278:2947-55.
Curran ME, Splawski I, Timothy KW, Vincent GM, Green ED and Keating MT. A molecular basis for cardiac arrhythmia: HERG mutations cause long QT syndrome. Cell. 1995;80:795-803.
Dodson MW, Brown LM and Elliott CG. Pulmonary Arterial Hypertension. Heart Fail Clin. 2018;14:255-269.
Dunham-Snary KJ, Wu D, Sykes EA, Thakrar A, Parlow LRG, Mewburn JD, Parlow JL and Archer SL. Hypoxic Pulmonary Vasoconstriction: From Molecular Mechanisms to Medicine. Chest. 2017;151:181-192.
EHealthMe. TIKOSYN and Pulmonary hypertension—from FDA reports eHealthMe. 2018;https://www.ehealthme.com/ds/tikosyn/pulmonary-hypertension/.
Farber HW and Loscalzo J. Pulmonary arterial hypertension. N Engl J Med. 2004;351:1655-65.
Farrelly AM, Ro S, Callaghan BP, Khoyi MA, Fleming N, Horowitz B, Sanders KM and Keef KD. Expression and function of KCNH2 (HERG) in the human jejunum. Am J Physiol Gastrointest Liver Physiol. 2003;284:G883-95.
Ficker E, Jarolimek W, Kiehn J, Baumann A and Brown AM. Molecular determinants of dofetilide block of HERG K+ channels. Circ Res. 1998;82:386-95.
Furlan F, Taccola G, Grandolfo M, Guasti L, Arcangeli A, Nistri A and Ballerini L. ERG conductance expression modulates the excitability of ventral horn GABAergic interneurons that control rhythmic oscillations in the developing mouse spinal cord. J Neurosci. 2007;27:919-28.

(Continued)

*Primary Examiner* — Rei Tsang Shiao
(74) *Attorney, Agent, or Firm* — Lathrop GPM; Judith L. Stone-Hulslander

(57) ABSTRACT

Provided are methods of treating pulmonary artery hypertension with a Kv11.1 (ERG or hERG1) channel inhibitor. In certain embodiments, the Kv11.1 channel inhibitor is dofetilide. In certain embodiments, a subject to be treated using a method of the disclosure is not in need of treatment for an irregular heart rhythm, e.g., atrial fibrillation.

12 Claims, 5 Drawing Sheets

(56) References Cited

PUBLICATIONS

Guasti L, Cilia E, Crociani O, Hofmann G, Polvani S, Becchetti A, Wanke E, Tempia F and Arcangeli A. Expression pattern of the ether-a-go-go-related (ERG) family proteins in the adult mouse central nervous system: evidence for coassembly of different subunits. J Comp Neurol. 2005;491:157-74.

Gullo F, Ales E, Rosati B, Lecchi M, Masi A, Guasti L, Cano-Abad MF, Arcangeli A, Lopez MG and Wanke E. ERG K+ channel blockade enhances firing and epinephrine secretion in rat chromaffin cells: the missing link to LQT2-related sudden death? FASEB J. 2003;17:330-2.

Higenbottam T. Pulmonary hypertension and chronic obstructive pulmonary disease: a case for treatment. Proc Am Thorac Soc. 2005;2:12-9.

Ibrahim YF, Shults NV, Rybka V and Suzuki YJ. Docetaxel Reverses Pulmonary Vascular Remodeling by Decreasing Autophagy and Resolves Right Ventricular Fibrosis. J Pharmacol Exp Ther. 2017;363:20-34.

Ibrahim YF, Wong CM, Pavlickova L, Liu L, Trasar L, Bansal G and Suzuki YJ. Mechanism of the susceptibility of remodeled pulmonary vessels to drug-induced cell killing. J Am Heart Assoc. 2014;3:e000520.

Jehle J, Schweizer PA, Katus HA and Thomas D. Novel roles for hERG K(+) channels in cell proliferation and apoptosis. Cell Death Dis. 2011;2:e193.

Kiehn J, Lacerda AE, Wible B and Brown AM. Molecular physiology and pharmacology of HERG. Single-channel currents and block by dofetilide. Circulation. 1996;94:2572-2579.

Kolbe K, Schonherr R, Gessner G, Sahoo N, Hoshi T and Heinemann SH. Cysteine 723 in the C-linker segment confers oxidative inhibition of hERG1 potassium channels. J Physiol. 2010;588:2999-3009.

Lamarca V, Grasa L, Fagundes DS, Arruebo MP, Plaza MA and Murillo MD. K+ channels involved in contractility of rabbit small intestine. J Physiol Biochem. 2006;62:227-36.

Lillich JD, Rakestraw PC, Roussel AJ, Finley MR, Ganta S and Freeman LC. Expression of the ether-a-go-go (ERG) potassium channel in smooth muscle of the equine gastrointestinal tract and influence on activity of jejunal smooth muscle. Am J Vet Res. 2003;64:267-72.

Lin H, Xiao J, Luo X, Wang H, Gao H, Yang B and Wang Z. Overexpression HERG K(+) channel gene mediates cell-growth signals on activation of oncoproteins SP1 and NF-kappaB and inactivation of tumor suppressor Nkx3.1. J Cell Physiol. 2007;212:137-47.

Madden JA, Dantuma MW, Sorokina EA, Weihrauch D and Kleinman JG. Telokin expression and the effect of hypoxia on its phosphorylation status in smooth muscle cells from small and large pulmonary arteries. Am J Physiol Lung Cell Mol Physiol. 2008;294:L1166-73.

Madden JA, Dawson CA and Harder DR. Hypoxia-induced activation in small isolated pulmonary arteries from the cat. J Appl Physiol (1985). 1985;59:113-8.

Madden JA, Ray DE, Keller PA and Kleinman JG. Ion exchange activity in pulmonary artery smooth muscle cells: the response to hypoxia. Am J Physiol Lung Cell Mol Physiol. 2001;280:L264-71.

Madden JA, Vadula MS and Kurup VP. Effects of hypoxia and other vasoactive agents on pulmonary and cerebral artery smooth muscle cells. Am J Physiol. 1992;263:L384-93.

Melnyk P, Ehrlich JR, Pourrier M, Villeneuve L, Cha TJ and Nattel S. Comparison of ion channel distribution and expression in cardiomyocytes of canine pulmonary veins versus left atrium. Cardiovasc Res. 2005;65:104-16.

Mewe M, Bauer CK, Schwarz JR and Middendorff R. Mechanisms regulating spontaneous contractions in the bovine epididymal duct. Biol Reprod. 2006;75:651-9.

Mewe M, Wulfsen I, Schuster AM, Middendorff R, Glassmeier G, Schwarz JR and Bauer CK. Erg K+ channels modulate contractile activity in the bovine epididymal duct. Am J Physiol Regul Integr Comp Physiol. 2008;294:R895-904.

Ohya S, Asakura K, Muraki K, Watanabe M and Imaizumi Y. Molecular and functional characterization of ERG, KCNQ, and KCNE subtypes in rat stomach smooth muscle. Am J Physiol Gastrointest Liver Physiol. 2002;282:G277-87.

Ohya S, Horowitz B and Greenwood IA. Functional and molecular identification of ERG channels in murine portal vein myocytes. Am J Physiol Cell Physiol. 2002;283:C866-77.

Oka M, Homma N, Taraseviciene-Stewart L, Morris KG, Kraskauskas D, Burns N, Voelkel NF and McMurtry IF. Rho kinase-mediated vasoconstriction is important in severe occlusive pulmonary arterial hypertension in rats. Circ Res. 2007;100:923-9.

Papa M, Boscia F, Canitano A, Castaldo P, Sellitti S, Annunziato L and Taglialatela M. Expression pattern of the ether-a-gogo-related (ERG) K+ channel-encoding genes ERG1, ERG2, and ERG3 in the adult rat central nervous system. J Comp Neurol. 2003;466:119-35.

Parr E, Pozo MJ, Horowitz B, Nelson MT and Mawe GM. ERG K+ channels modulate the electrical and contractile activities of gallbladder smooth muscle. Am J Physiol Gastrointest Liver Physiol. 2003;284:G392-8.

Sacco T, Bruno A, Wanke E and Tempia F. Functional roles of an ERG current isolated in cerebellar Purkinje neurons. J Neurophysiol. 2003;90:1817-28.

Sanguinetti MC, Jiang C, Curran ME and Keating MT. A mechanistic link between an inherited and an acquired cardiac arrhythmia: HERG encodes the IKr potassium channel. Cell. 1995;81:299-307.

Sanguinetti MC, Jurkiewicz NK, Scott A and Siegl PK. Isoproterenol antagonizes prolongation of refractory period by the class III antiarrhythmic agent E-4031 in guinea pig myocytes. Mechanism of action. Circ Res. 1991;68:77-84.

Sato K, Webb S, Tucker A, Rabinovitch M, O'Brien RF, McMurtry IF and Stelzner TJ. Factors influencing the idiopathic development of pulmonary hypertension in the fawn hooded rat. Am Rev Respir Dis. 1992;145:793-7.

Schonherr R and Heinemann SH. Molecular determinants for activation and inactivation of HERG, a human inward rectifier potassium channel. J Physiol. 1996;493 ( Pt 3):635-642.

Shi W, Wymore R, Yu H, Wu J, Wymore RT, Pan Z, Robinson RB, Dixon JE, McKinnon D and Cohen IS. Distribution and prevalence of hyperpolarization-activated cation channel (HCN) mRNA expression in cardiac tissues. Circ Res. 1999;85:e1-e6.

Shujaat A, Minkin R and Eden E. Pulmonary hypertension and chronic cor pulmonale in COPD. Int J Chron Obstruct Pulmon Dis. 2007;2:273-82.

Smith GA, Tsui HW, Newell EW, Jiang X, Zhu XP, Tsui FW and Schlichter LC. Functional up-regulation of HERG K+ channels in neoplastic hematopoietic cells. J Biol Chem. 2002;277:18528-34.

Smith PL, Baukrowitz T and Yellen G. The inward rectification mechanism of the HERG cardiac potassium channel. Nature. 1996;379:833-836.

Spector PS, Curran ME, Keating MT and Sanguinetti MC. Class III antiarrhythmic drugs block HERG, a human cardiac delayed rectifier K+ channel. Open-channel block by methanesulfonanilides. Circ Res. 1996;78:499-503.

Taglialatela M, Pannaccione A, Iossa S, Castaldo P and Annunziato L. Modulation of the K(+) channels encoded by the human ether-a-gogo-related gene-1 (hERG1) by nitric oxide. Mol Pharmacol. 1999;56:1298-308.

Titus SA, Warmke JW and Ganetzky B. The *Drosophila* erg K+ channel polypeptide is encoded by the seizure locus. J Neurosci. 1997; 17:875-81.

Trudeau MC, Warmke JW, Ganetzky B and Robertson GA. HERG, a human inward rectifier in the voltage-gated potassium channel family. Science. 1995;269:92-95.

Vadula MS, Kleinman JG and Madden JA. Effect of hypoxia and norepinephrine on cytoplasmic free Ca2+ in pulmonary and cerebral arterial myocytes. Am J Physiol. 1993;265:L591-7.

Vandenberg JI, Perry MD, Perrin MJ, Mann SA, Ke Y and Hill AP. hERG K(+) channels: structure, function, and clinical significance. Physiol Rev. 2012;92:1393-1478.

Weir EK and Olschewski A. Role of ion channels in acute and chronic responses of the pulmonary vasculature to hypoxia. Cardiovasc Res. 2006;71:630-41.

(56) References Cited

PUBLICATIONS

Wymore RS, Gintant GA, Wymore RT, Dixon JE, McKinnon D and Cohen IS. Tissue and species distribution of mRNA for the IKr-like K+ channel, erg. Circ Res. 1997;80:261-8.
Zhou Z, Gong Q, Epstein ML and January CT. HERG channel dysfunction in human long QT syndrome. Intracellular transport and functional defects. J Biol Chem. 1998;273:21061-21066.
Zhu Y, Golden CM, Ye J, Wang XY, Akbarali HI and Huizinga JD. ERG K+ currents regulate pacemaker activity in ICC. Am J Physiol Gastrointest Liver Physiol. 2003;285:G1249-58.

\* cited by examiner

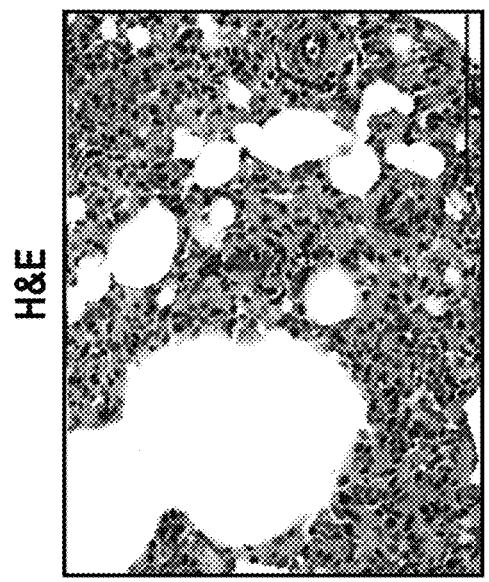
Fig. 4A H&E
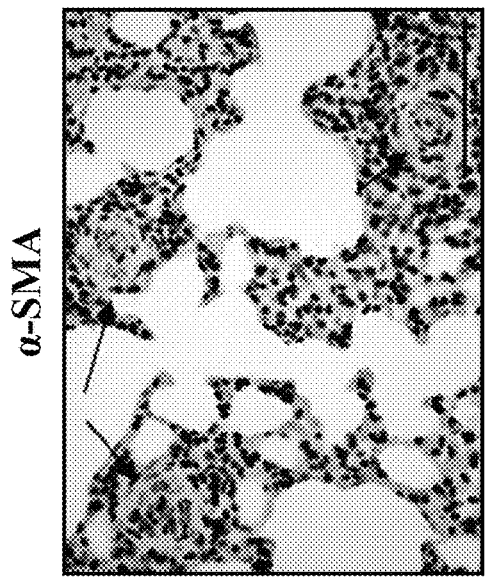
Fig. 4B α-SMA
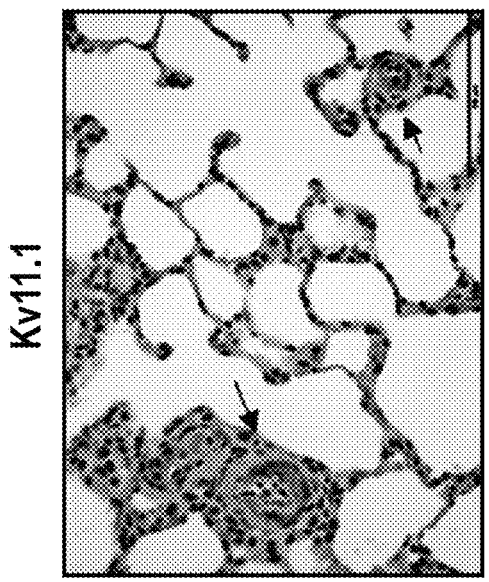
Fig. 4C Kv11.1
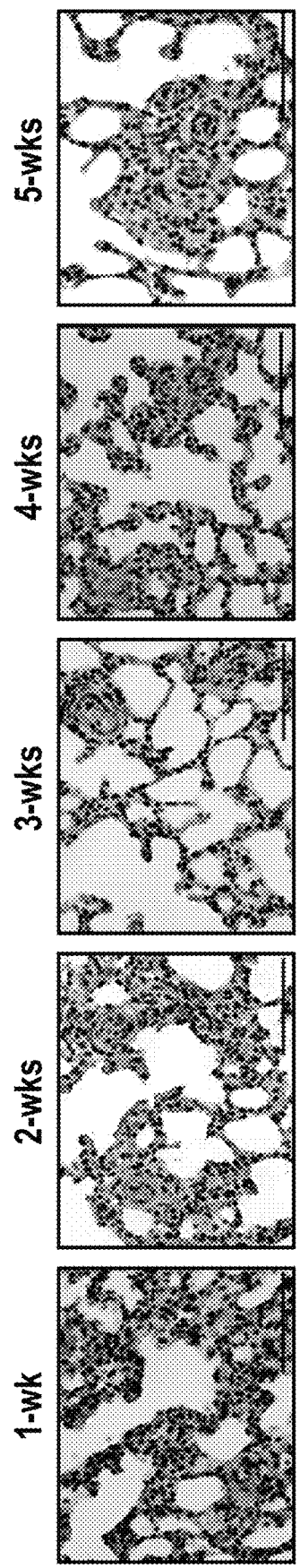
Fig. 5
1-wk  2-wks  3-wks  4-wks  5-wks

USE OF KV11.1 CHANNEL INHIBITORS FOR TREATMENT OF PULMONARY HYPERTENSION

RELATED APPLICATION

This application claims benefit of U.S. Provisional Patent Application No. 62/852,020, filed May 23, 2019, the entire contents of which are incorporated herein by reference.

STATEMENT OF GOVERNMENT SUPPORT

This invention was made with government support under GM124020 and HL072844 awarded by the National Institutes of Health. The government has certain rights in the invention.

BACKGROUND OF THE INVENTION

Kv11.1 potassium-selective channels, also known as EAG-related gene (ERG) channels, or hERG1 channels, are best known for their function in the heart where they are responsible for the repolarization of the cardiac action potential[1-4]. Inhibition of Kv11.1 currents due to genetically occurring mutations or as a side effect of a prescription medication lengthens the QT interval in electrocardiogram, causing long-QT syndrome (LQTS), a potentially lethal cardiac arrhythmia[5-8]. Kv11.1 channels also play a role in cancer, where inhibition of Kv11.1 channel expression and/or Kv11.1 currents decreases proliferation of cancer cells[9, 10]. In addition to cardiac tissue, Kv11.1 channels are also expressed in the brain[11, 12], retina[13], gallbladder[14], stomach[15] and intestines[16-18]. However, surprisingly little is known about the Kv11.1 channel expression and function in normal lung tissue.

Potassium channels are essential for proper lung function, and defects in ion channels are linked to various respiratory diseases[19]. Potassium channels are especially intimately involved in vascular remodeling in pulmonary hypertension, and associated respiratory diseases such as pulmonary arterial hypertension (PAH) and chronic obstructive pulmonary disease (COPD)[20-22].

PAH is a lethal disease associated with narrowing arteries in the lung[23, 24]. The constriction of the arteries decreases blood flow through the lungs and leads to decreased oxygen levels in the blood. Although with current treatments the symptoms of PAH can be relieved, there is no known cure[23, 24]. Similar to PAH, COPD-associated pulmonary hypertension also results in the constriction of arteries in the lung.

Several types of potassium channels have been implicated in the vascular remodeling in PAH and COPD, including BK channels, $K_{ATP}$ channels, and two-pore domain potassium channels[26]. It is thought that the decrease in currents through potassium channels in response to hypoxia leads to cell depolarization that increases $Ca^{2+}$ influx through voltage-gated calcium channels, causing vasoconstriction[26, 27].

Despite the importance of Kv11.1 channels for many physiological processes, their expression and function in pulmonary vasculature and potential role in PAH- and COPD-associated vascular remodeling has not been investigated.

SUMMARY OF THE INVENTION

The present invention is based at least in part on the discovery by the instant inventors that Kv11.1 channels are expressed in the lung vasculature of healthy humans and rats. The Kv11.1 expression was detected in large pulmonary arteries with the diameter of ≥100 μm and was undetectable in smaller diameter arteries for both healthy humans and rats. In humans with COPD-associated pulmonary hypertension and rats with PAH, Kv11.1 channel expression level increased and was detected not only in the large diameter arteries but also smaller arteries with the diameter of ≤100 μm. The increase in the Kv11.1 channel expression level closely followed the time course of the vascular remodeling in PAH-induced rats. Surprisingly, treatment of PAH-induced rats with Kv11.1 channel-specific blocker dofetilide, clinically known as an antiarrhythmic drug TIKOSYN® (dofetilide), decreased the PAH-associated remodeling by increasing the arterial lumen opening and decreasing the arterial wall thickness. Taken together, these findings identified Kv11.1 channels as important players in the function of healthy and pulmonary hypertension-affected lungs in humans and rats. Therefore, Kv11.1 channels should be considered as novel drug targets for treatment of pulmonary hypertension. Moreover, Kv11.1 channel blocker dofetilide may have a potential for PAH treatment.

An aspect of the invention is a method of treating pulmonary artery hypertension, comprising administering to a subject in need thereof an effective amount of a Kv11.1 channel inhibitor.

In certain embodiments, the pulmonary artery hypertension is not associated with chronic obstructive pulmonary disease (COPD).

In certain embodiments, the pulmonary artery hypertension is associated with chronic obstructive pulmonary disease (COPD).

In certain embodiments, the subject is not in need of treatment for irregular heart rhythm.

In certain embodiments, the subject is not in need of treatment for atrial fibrillation.

In certain embodiments, the subject is a human.

In certain embodiments, the Kv11.1 inhibitor is dofetilide.

BRIEF DESCRIPTION OF THE DRAWINGS

FIGS. 1E and 1F show Kv11.1-negative cells in small pulmonary arterioles (<100 μm diameter) (arrows). FIGS. 1A and 1B, bar=1 mm. FIGS. 1C-1F, bar=200 μm.

FIG. 2A shows H&E staining of lung tissue; bar=1 mm. FIG. 2B shows positive Kv11.1 antibody staining of media of large pulmonary arteries (>100 μm diameter, asterisk), and of small pulmonary arteries (<100 μm diameter, arrows); bar=200 μm.

FIG. 3A shows H&E staining of lung tissue showing a normal structure of a bronchiole (b), thin interstitial alveolar wall (magnification ×200), and normal arterial wall thickness (arrow, magnification ×400) in control rats. FIG. 3B shows anti-smooth muscle actin (anti-SMA) antibody staining in the smooth muscle cell (SMC) layer of a bronchiole (asterisk) and in the media of pulmonary arteries (asterisk, >100 μm in diameter). Image in ×400 magnification shows no expression of anti-SMA in small pulmonary arteries (<100 μm in diameter). FIG. 3C shows Kv11.1 antibody staining in bronchial SMC layer (asterisk) and in the media of pulmonary arteries (asterisk, >100 μm in diameter). Image in ×400 magnification illustrates Kv11.1-negative cells of small pulmonary arterioles (arrows). FIGS. 3A-3C, left-hand images, bar=200 μm; right-hand images, bar=100 μm.

FIGS. 4A-4C: Kv11.1 channel expression in PAH-induced rats. FIG. 4A shows H&E staining of lung tissue of PAH-induced Fisher rats. After SU5416 injection the rats were kept in hypoxia for 3 weeks and then maintained in normoxia for 5 weeks. FIG. 4B shows anti-SMA antibody staining in the media of small pulmonary arteries (arrows). FIG. 4C shows Kv11.1 antibody staining in the media of small pulmonary arteries (arrows). Magnification ×400. FIGS. 4A-4C, bar=100 μm.

FIG. 5: Time course examination of Kv11.1 expression in PAH-induced rats. For this experiment Fischer rats were injected with SU5416, placed in hypoxia for 3 weeks and then maintained in normoxia for 2 weeks to obtain time points of 0, 1, 2, 3, 4 and 5 weeks after the SU5416 injection. Bars=100 μm.

FIG. 6A shows representative images of pulmonary vessels of control, PAH-induced, and PAH-induced and dofetilide-treated rats (H&E stain at ×1000 magnifications). Bars=50 μm. FIG. 6B shows mean pulmonary arterial wall thickness (%). Error bars correspond to standard error of the mean (SEM). Lines above the bars in the graph denote significant differences from each other at $P<0.05$.

DETAILED DESCRIPTION OF THE INVENTION

Figure 1A:
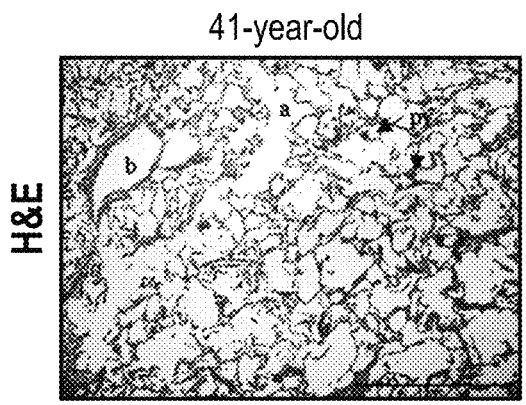
FIGS. 1A-1F: Histological examinations of lung structure of healthy humans of different age. Normal human lung hematoxylin and eosin (H&E) staining for a 41-year-old (FIG. 1A) and 65-year-old (FIG. 1B) individuals. Shown are sections of lung composed of terminal bronchioles (b) and thin-walled alveoli (a). Also shown is a thin layer of alveoli connective tissue and a multitude of pulmonary vessels (pv, arrows). Images display Kv11.1-positive cells in bronchial smooth muscle layer (asterisk) and in the media of pulmonary arteries >100 μm in diameter (asterisk) in the 41-year-old (FIG. 1C) and 65-year-old (FIG. 1D) individuals.

Kv11.1 potassium selective channels are essential for the heart repolarization. Prescription medication that blocks Kv11.1 channels lengthens the ventricular action potential and causes cardiac arrhythmias. Surprisingly, little is known about the Kv11.1 channel expression and function in the lung tissue. As disclosed herein, Kv11.1 channel expression in healthy and pulmonary hypertension-affected human and rat lungs was investigated, and the effect of Kv11.1 channel-specific blocker dofetilide, also known as antiarrhythmic drug TIKOSYN®, on vascular remodeling in pulmonary arterial hypertension (PAH) was tested.

Kv11.1 channel expression in human postmortem tissue from healthy individuals and patients with chronic obstructive pulmonary disease (COPD)—associated pulmonary hypertension, and in rat smooth muscle cells (SMCs) from healthy and PAH-induced animals was detected with Kv11.1-specific antibody. While in healthy human and rat lung tissues Kv11.1 channels were expressed in the SMCs of large pulmonary arteries, in humans with COPD-associated pulmonary hypertension and rats with PAH, Kv11.1 channels were expressed not only in the large pulmonary arteries but also in small pulmonary arteries. The increase in the expression of Kv11.1 channels closely followed the time course of the development of pulmonary vascular remodeling in PAH-induced rats. Treatment of PAH-induced rats with Kv11.1 channel blocker dofetilide inhibited PAH-associated pulmonary vascular remodeling while having no effect on the pulmonary vasculature of control rats.

The present inventors believe they are the first to report abundant expression of Kv11.1 channels in the large pulmonary arteries of healthy human and rat lung tissues. Kv11.1 channel expression increased in human lungs affected by COPD and in lungs of PAH-induced rats, indicating the importance of Kv11.1 channels for lung function and their potential as new drug targets in the treatment of pulmonary hypertension. Kv11.1 channel blocker dofetilide reversed the vascular remodeling in PAH-induced rats. The protective effect of dofetilide in PAH-induced rats raises the possibility of repurposing this antiarrhythmic drug for the treatment of patients with pulmonary hypertension.

Pulmonary arterial hypertension (PAH) is one form of a broader condition known as pulmonary hypertension, which means high blood pressure in the lungs. In PAH, increased pressure in the vessels is caused by obstruction in the small arteries in the lung, for any of a variety of reasons. In many cases of pulmonary arterial hypertension, the cause is unknown (idiopathic); other causes can be drug-related, HIV infection; connective tissue/autoimmune disorders (such as scleroderma), and others.

Individuals with PAH may go years without a diagnosis, either because their symptoms are mild, nonspecific, or only present during demanding exercise. Although limited treatments for PAH are available, it is still considered an incurable disease. It is important to treat PAH because without treatment, high blood pressure in the lungs causes the right heart to work much harder, and over time, this heart muscle may weaken or fail. The progressive nature of this disease means that an individual may experience only mild symptoms at first, but will eventually require treatment and medical care to maintain a reasonable quality of life.

PAH symptoms are those that are usually due to not having enough oxygen in the blood. In most cases, the initial symptom is severe shortness of breath following exertion. Additional symptoms include excessive fatigue, weakness, chest pain, dizzy spells, and fainting episodes.

Affected individuals may also have a cough, sometimes with blood (hemoptysis), an enlarged heart and liver, low systemic blood pressure (hypotension), and hoarseness due to compression of a nerve in the chest by an enlarged pulmonary artery.

Some affected individuals may experience puffiness or swelling of the face, ankles, abdomen and feet due to abnormal accumulation of fluid (edema) within fascial tissues.

Individuals with advanced stages of PAH may have abnormal bluish discoloration of the skin due to low levels of circulating oxygen in the blood (cyanosis). In addition, in severe cases of PAH, the right chamber (ventricle) of the heart is abnormally enlarged (hypertrophied), resulting in diminished functioning of the right portion of the heart and, potentially, right-sided heart failure. Some patients with PAH do not seek medical advice until they are no longer able to continue with their normal activities. At this time, the disease may have progressed to a point where the patient is completely bedridden from shortness of breath or other symptoms.

The diagnosis of PAH is frequently one of exclusion, meaning that PAH is only diagnosed when other causes of signs or symptoms of pulmonary hypertension have been ruled out and there seems to be no known cause of the hypertension. The tests that are commonly performed to diagnose PAH and rule out other diseases are echocardiography, blood tests, pulmonary function tests, X-rays of the chest, electrocardiography (ECG), and the "6-minute walk test", which essentially measures how far an individual can walk in that time period. Ultimately, the majority of subjects undergo confirmation by cardiac catheterization with and without vasodilator testing.

Several medications have been approved by the US Food and Drug Administration (FDA) for the treatment of PAH. These medications can be broadly broken down into four categories described below—prostaglandins, endothelin receptor antagonists, phosphodiester type 5 inhibitors, and supportive therapies.

Prostaglandins

The orphan drug FLOLAN® (epoprostenol sodium for injection or prostacyclin) has been approved as a standard long-term treatment of individuals with severe PAH. It was the first drug approved specifically for patients with pulmonary hypertension. This drug is used in individuals who do not respond to other types of therapy and in patients with very severe disease. This drug is administered by intravenous infusion through a permanent ambulatory in-dwelling central venous catheter. Since this drug requires continuous infusion, it must not be withdrawn suddenly (including sudden reduction of dosage). FLOLAN®, which is a version of a natural hormone called prostacyclin that dilates constricted blood vessels, is manufactured by GlaxoSmithKline.

Recently, a room temperature stable form of epoprostenol had been developed. This is known as VELETRI® and is made by Actelion Pharmaceuticals US, Inc.

The FDA has approved the orphan drug REMODULIN® (treprostinil) in subcutaneous and intravenous forms and TYVASO®, an inhaled form of treprostinil, and oral form (ORENITRAM®) for the treatment of PAH. The drug is made by United Therapeutics Corp.

In 2004, the FDA approved VENTAVIS® (iloprost) for the treatment of PAH. The treatment is inhaled through the mouth with the assistance of a special nebulizer, dilating the arteries and preventing the formation of blood clots. VENTAVIS® is marketed in the U.S. by Actelion Pharmaceuticals US, Inc.

Endothelin Receptor Antagonists

The orphan drug TRACLEER® (bosentan) has been approved by the FDA for treatment of PAH. The drug allows affected individuals to exert themselves physically without shortness of breath. It should be carefully monitored while in use. TRACLEER® is manufactured by Actelion Pharmaceuticals US, Inc.

The FDA has approved the orphan drug LETAIRIS® (ambrisentan) for treatment of PAH in June 2007. It is used primarily to make exercise and breathing easier. Because of the risk of birth defects, ambrisentan is available only through a special restricted distribution program called the Letairis Education and Access Program (LEAP).

The FDA has approved the orphan drug OPSUMIT® (macitentan) for treatment of PAH in October 2013. In clinical trials this drug was shown to delay disease progression. It works through similar mechanisms as bosentan and ambrisentan. Macitentan is manufactured by Actelion Pharmaceuticals US, Inc.

Phosphodiesterase Type 5 Inhibitors

REVATIO® (sildenafil), a phosphodiesterase type 5 (PDE5) inhibitor, is also used to treat PAH. In clinical studies it increased the distance people walked and decreased pressure in the pulmonary artery. It contains the same ingredient as VIAGRA® (sildenafil citrate). This medication is manufactured by Pfizer Pharmaceuticals.

ADCIRCA® (tadalafil) is a once-daily phosphodiesterase type 5 (PDE5) inhibitor, shown to improve the patient's ability to exercise. ADCIRCA® contains the same active ingredient (tadalafil) as CIALIS®. This medication is available from United Therapeutics.

The FDA has approved the drug ADEMPAS® (riociguat) for the treatment of PAH. Riociguat works on the same pathway as the phosphodiesterase type 5 inhibitors. This medication is made by Bayer.

In 2016, UPTRAVI® (selexipag) was approved for adults and acts by relaxing muscles in the walls of blood vessels. UPTRAVI®is manufactured by Actelion Pharmaceuticals US, Inc.

Supportive Therapies

Drugs that cause widening of blood vessels (vasodilators) and lessen blood pressure may also be used to treat PAH. In some PAH cases, calcium channel blockers (e.g., nifedipine and diltiazem) are used as vasodilators. Unfortunately, only a small minority of patients appear to respond with improvement to the use of calcium channel blockers. Other vasodilator drugs have been used including phentolamine, phenoxybenzamine and prazosin. The effectiveness of vasodilator therapy varies from case to case.

Other treatments such as anticoagulants, diuretics, and oxygen may be used to treat PAH as supportive therapies. Anticoagulants, such as warfarin, are drugs that prevent blood clots from forming. There are equivocal data on whether these drugs are useful in PAH patients and there are significant bleeding risks associated with them. Diuretics are used to treat fluid retention and swelling (edema) often associated with the condition.

Kv11.1 channel inhibitors include, without limitation, dofetilide, haloperidol, terfenadine, astemizole, cisapride, and amiodarone. Additional Kv11.1 channel inhibitors include blocking antibodies, and antigen-binding fragments thereof, which bind specifically to Kv11.1 or hERG and inhibit its function, e.g., repolarization of cardiac action potential.

An aspect of the invention is a method of treating pulmonary artery hypertension, comprising administering to a subject in need thereof an effective amount of a Kv11.1 channel inhibitor.

In certain embodiments, the pulmonary artery hypertension is not associated with chronic obstructive pulmonary disease (COPD).

In certain embodiments, the pulmonary artery hypertension is associated with chronic obstructive pulmonary disease (COPD).

In certain embodiments, the subject is not in need of treatment for irregular heart rhythm.

In certain embodiments, the subject is not in need of treatment for atrial fibrillation.

In certain embodiments, the subject is a human.

In certain embodiments, the Kv11.1 inhibitor is dofetilide.

In certain embodiments, the Kv11.1 inhibitor is administered orally. In certain embodiments, the Kv11.1 inhibitor is administered parenterally, e.g., intravenously or intraperitoneally. In certain embodiments, the Kv11.1 inhibitor is administered directly to lungs, e.g., intratracheally or by inhalation.

In some embodiments, the Kv11.1 inhibitor is administered in conjunction with standard-of-care treatment of pulmonary artery hypertension, e.g., prostaglandins, endothelin receptor antagonists, phosphodiesterase type 5 inhibitors, and/or supportive therapies.

EXAMPLES

Methods

Human Tissues

10% Formalin-fixed and paraffin-embedded lung tissues from healthy control subjects and patients with COPD were purchased from National Disease Research Interchange (Philadelphia, Pa., USA).

Animal Treatment

Male SD and Fischer rats were purchased from Charles River Laboratories International, Inc., (Wilmington, Mass., USA). To induce PAH, rats were subcutaneously injected with 20 mg/kg body weight SU5416 (inhibitor of vascular endothelial growth factor (VEGF) receptor Flk/1-KDR; MedChemExpress, Monmouth Junction, N.J., USA) and maintained in hypoxia[28-30]. For hypoxia, animals were placed in a chamber (30" w×20" d×20" h) regulated by an OxyCycler Oxygen Profile Controller (Model A84XOV; BioSpherix, Redfield, N.Y., USA) set to maintain 10% $O_2$ with an influx of $N_2$ gas, located in the animal care facility at the Georgetown University Medical Center. Ventilation to the outside of the chamber was adjusted to remove $CO_2$, such that its level did not exceed 5,000 ppm. Animals were fed normal rat chow.

In a first experiment to determine the effects of a Kv11.1 inhibitor (dofetilide), SD rats were divided into 4 groups that were treated with (1) DMSO, (2) dofetilide, (3) DMSO+SU5416/Hypoxia, and (4) dofetilide+SU5416/Hypoxia, respectively (n=4 for each group). Dofetilide (10 mg/kg body weight) was dissolved in DMSO and injected intraperitoneally before the injection of SU5416. For histological examination, lung tissues were fixed in 10% formalin and embedded in paraffin. The Georgetown University Animal Care and Use Committee approved all animal experiments, and the investigation conformed to the National Institutes of Health Guide for the Care and Use of Laboratory Animals.

In a second experiment to determine the effects of dofetilide, SD rats are divided into 4 groups that are treated with (1) DMSO, (2) dofetilide, (3) DMSO+SU5416/Hypoxia, and (4) dofetilide+SU5416/Hypoxia, respectively (n=4 for each group). Dofetilide (1000 μg/kg body weight) is dissolved in DMSO and injected intraperitoneally before the injection of SU5416. For histological examination, lung tissues are fixed in 10% formalin and embedded in paraffin.

In a third experiment to determine the effects of dofetilide, SD rats are divided into 4 groups that are treated with (1) DMSO, (2) dofetilide, (3) DMSO+SU5416/Hypoxia, and (4) dofetilide+SU5416/Hypoxia, respectively (n=4 for each group). Dofetilide (100 μg/kg body weight) is dissolved in DMSO and injected intraperitoneally before the injection of SU5416. For histological examination, lung tissues are fixed in 10% formalin and embedded in paraffin.

In a fourth experiment to determine the effects of dofetilide, SD rats are divided into 4 groups that are treated with (1) DMSO, (2) dofetilide, (3) DMSO+SU5416/Hypoxia, and (4) dofetilide+SU5416/Hypoxia, respectively (n=4 for each group). Dofetilide (10 μg/kg body weight) is dissolved in DMSO and injected intraperitoneally before the injection of SU5416. For histological examination, lung tissues are fixed in 10% formalin and embedded in paraffin.

Histological Measurements

Paraffin-embedded tissues were cut and mounted on glass slides. Tissue sections were subjected to hematoxylin and eosin (H&E) stain and immunohistochemistry using anti-smooth muscle actin (anti-SMA) antibody (Abcam, Cambridge, UK) and Kv11.1 antibody (Alomone Labs, Jerusalem, Israel).

Morphometric Analysis

Lung slides were analyzed for pulmonary artery wall thickness. 30 vessels were analyzed per animal in each group, and four values of external and internal diameters for thickness were measured for each vessel. The wall thickness was calculated as difference of external and internal diameters by using Fiji software.

Statistical Analysis

Means±SEM were calculated and then comparisons between two groups were analyzed using a two-tailed Student's t test, while comparisons between three or more groups were analyzed using ANOVA with a Student-Newman-Keuls post-hoc test. $P<0.05$ was considered to be significant.

Example 1

Figure 1B:
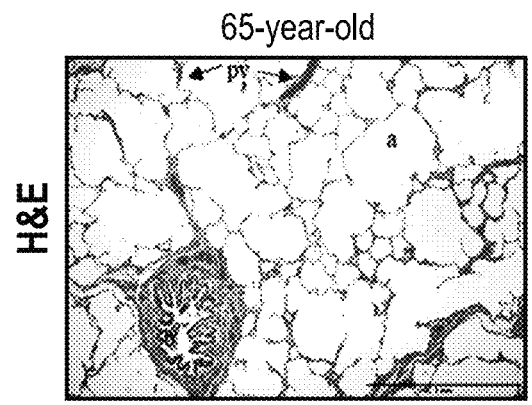
Figure 1C:
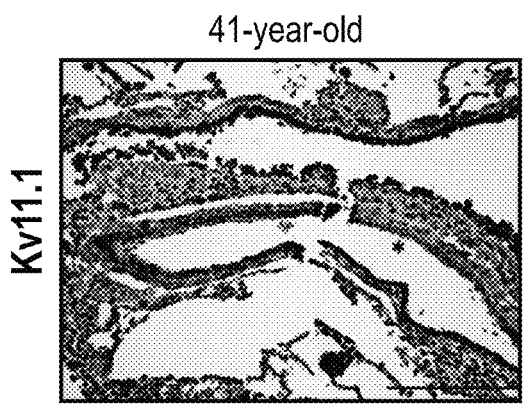
Figure 1D:
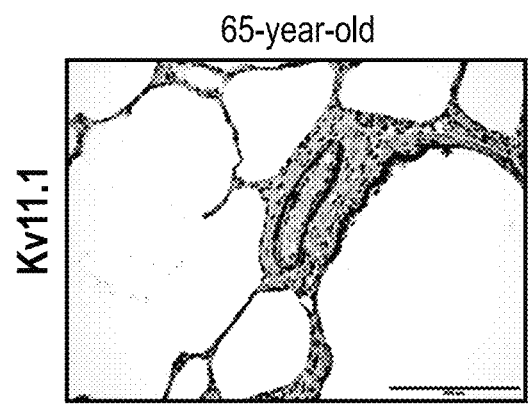
Figure 1E:
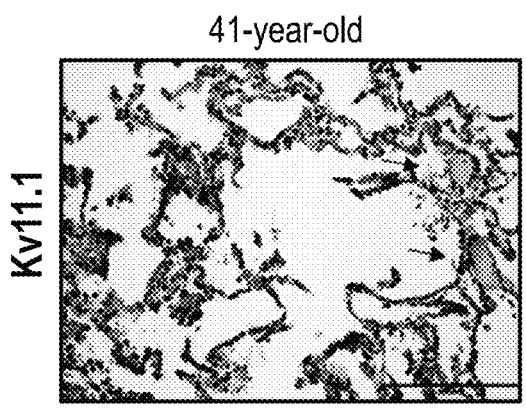
Figure 1F:
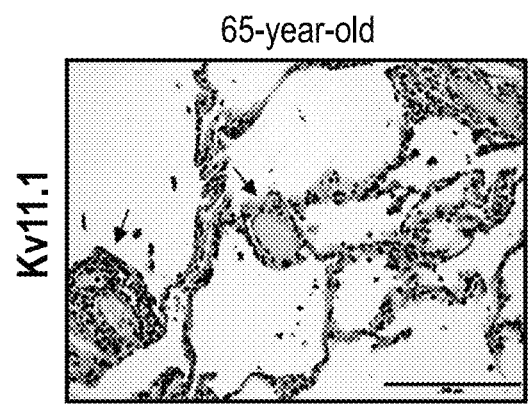

Kv11.1 Channels are Expressed in SMCs of Large Pulmonary Arteries in Lungs of Healthy Humans To investigate Kv11.1 channel expression in human lungs, histological examination of H&E-stained postmortem lung tissue from two healthy individuals, 41 (FIG. 1A) and 65 (FIG. 1B) years of age, was made. The examination revealed a normal lung structure with bronchiole, alveoli, thin layer of a connective tissue between the alveoli and a multitude of pulmonary vessels (FIGS. 1A and 1B). Immunohistochemical analysis with Kv11.1 channel antibody revealed a robust expression of Kv11.1 channels in the SMC layer of bronchiole and large diameter pulmonary arteries in lungs of both examined individuals (FIGS. 1C and 1D). No expression of Kv11.1 channels was detected in the small pulmonary arteries with the diameter of <100 μm for both examined individuals (FIGS. 1E and 1F).

Example 2

Figure 2A:
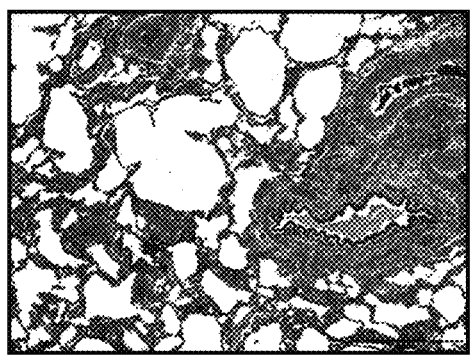
FIGS. 2A-2B: Histological examinations of lung structure of a 65-year-old human individual with COPD.
Figure 2B:
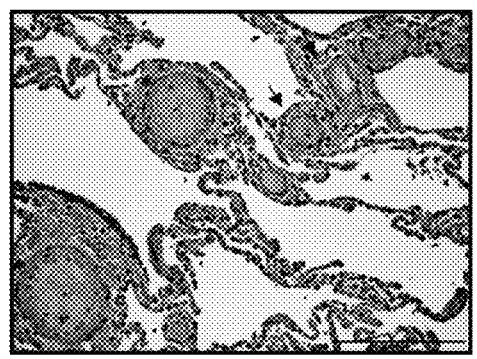

Kv11.1 Channels are Expressed in SMCs of Small Pulmonary Arteries of Humans with COPD To determine if the Kv11.1 channel expression level is altered in respiratory disease, the channel expression in a postmortem human lung tissue from a 65-year-old individual with COPD-associated pulmonary hypertension was examined. H&E staining revealed emphysematous distention and collapse of alveoli. Mild edema of the arterial wall, and peribronchial and perivascular fibrosis and thickening of walls of pulmonary arteries were observed (FIG. 2A). Immunohistochemical analysis of the COPD-affected lung with Kv11.1 channel antibody revealed a robust expression of Kv11.1 channels not only in the media of large pulmonary arteries with the diameter of >100 μm but also small pulmonary arteries with the diameter of <100 μm (FIG. 2B).

Example 3

Figure 3A:
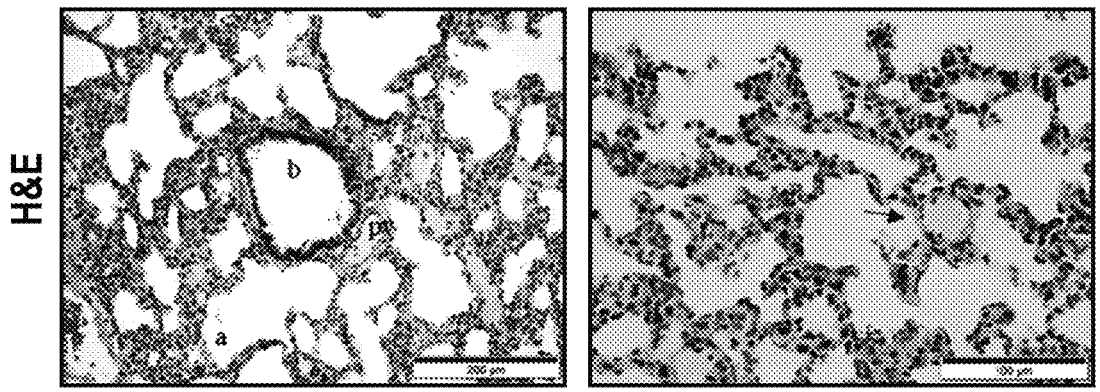
FIGS. 3A-3C: Histological examinations of lung structure of control Fischer rats. Normal lung parenchyma with a bronchiole (b), alveoli (a), alveolar walls and different diameter pulmonary vessels (pv).
Figure 3B:
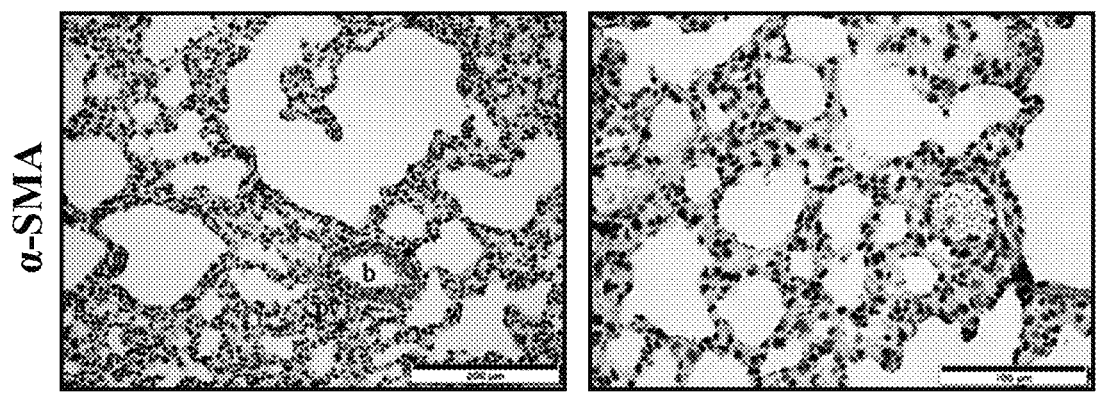
Figure 3C:
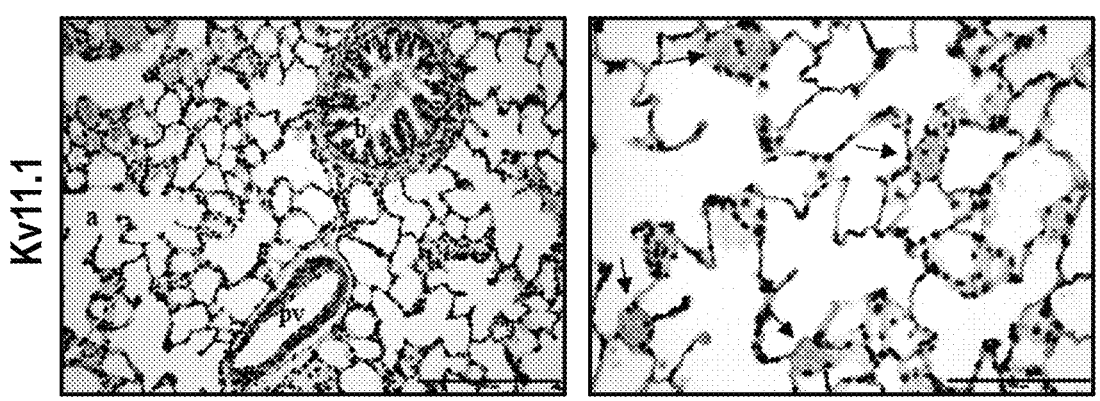

Kv11.1 Channels are Expressed in SMCs of Large Pulmonary Arteries in Lungs of Healthy Rats To determine if the Kv11.1 channel expression observed in healthy human lungs is also present in rat lungs, histological examination of the H&E-stained lung tissue of healthy Fisher rats was performed. The examination revealed lung parenchyma with bronchioles, alveoli, and different diameter pulmonary vessels of expected sizes (FIG. 3A). Immunohistochemical analysis with anti-SMA antibody indicated a typical SMC layer of a bronchiole and large pulmonary arteries and absence of the smooth muscle cell expression in the small pulmonary arteries with the diameter of <100 μm (FIG. 3B). Kv11.1 channel expression in healthy rat lung tissue was then examined with the Kv11.1 channel antibody. Immunohistochemical analysis revealed a robust Kv11.1 expression in the SMC layer of bronchiole and large diameter pulmonary arteries (FIG. 3C, left panel). No Kv11.1 channel expression was detected in the small pulmonary arteries with the diameter of <100 μm (FIG. 3C, right panel), similar to the absence of Kv11.1 channel expression in small arteries observed in human lungs. Similar results were obtained from immunohistochemical analysis of lung tissue from 4 different rats.

Example 4

Kv11.1 Channels are Expressed in SMCs of Large and Small Pulmonary Arteries in Rats with PAH This example examined if, similar to the COPD-associated with pulmonary hypertension in humans, Kv11.1 expression is altered in PAH-induced rats. To induce PAH, Fisher rats were injected with SU5416, placed in hypoxia for 3 weeks, and then maintained in normoxia (room air) for 5 weeks. The animals were then euthanized and histological data were obtained.

Histological examination of the H&E-stained lung tissue revealed alterations in the lung structure with PAH, including medial hypertrophy and alveolar wall thickening due to the endothelial cell proliferation (FIG. 4A). These changes led to the narrowing or occlusion of lumens of pulmonary arteries. Immunohistochemical analysis with the anti-SMA antibody indicated proliferation of SMCs and muscularization of the small diameter (<100 μm) pulmonary arteries (FIG. 4B), not seen in normal lung tissue (FIG. 3B). Immunohistochemical analysis with Kv11.1 antibody revealed Kv11.1 channel expression in smooth muscle cells of large and small pulmonary arteries (FIG. 4C), not observed in the normal tissue (FIG. 3C). The appearance of Kv11.1 channels in small diameter arteries in rats with PAH was similar to those observed in human lungs with COPD (FIG. 2).

The time course of changes in Kv11.1 channel expression with the PAH-associated vascular remodeling was monitored at 1, 2, 3, 4 and 5 weeks of normoxia following 3 weeks in hypoxia. The increase in the Kv11.1 channel expression and Kv11.1 channel appearance in small diameter pulmonary arteries closely followed the time course of the vascular remodeling in PAH and associated increased muscularization (FIG. 5).

Example 5

Figure 6A:
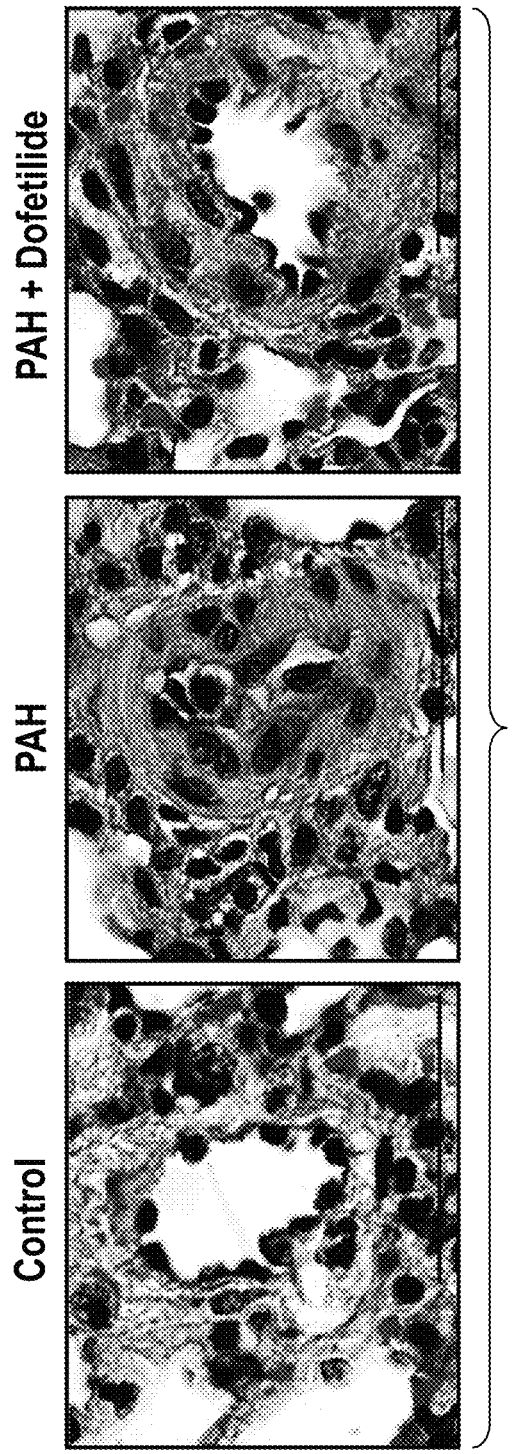
FIGS. 6A-6B: Histological examinations of pulmonary vessels.
Figure 6B:
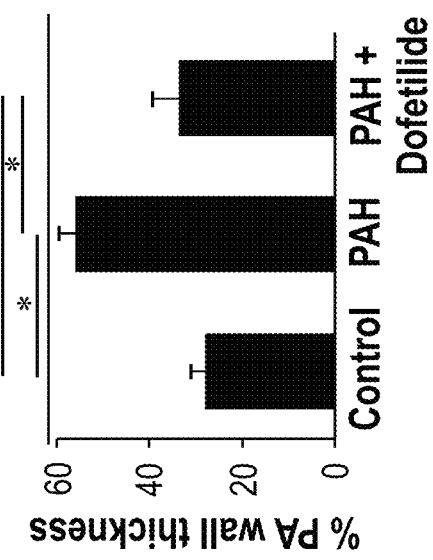

Kv11.1 Channel Blocker Dofetilide Reverses Pulmonary Artery Wall Remodeling of PAH-Induced Rats To determine if pharmacological inhibition of Kv11.1 channels would affect PAH progression, healthy and PAH-induced SD rats were treated with Kv11.1 channel-specific blocker dofetilide. Lung tissues from four groups of SD rats (four rats in each group) were examined with H&E staining. The rats in two control groups, group (1) injected with DMSO and group (2) injected with dofetilide, had similar lung structure and no statistical differences in small pulmonary arterial media wall thickness (SPAMWT), data not shown. PAH-induced rats in group (3) had increased intimal endothelial cell proliferation, increased SPAMWT, and reduced pulmonary arterial lumen diameter compared to control rats (FIGS. 6A and 6B). Surprisingly, PAH-induced, dofetilide-treated rats in group (4) had reduced SPAMWT and increased pulmonary arterial lumen diameter compared with PAH-induced rats in group (3) (FIGS. 6A and 6B). Remarkably, dofetilide completely eliminated PAH-induced changes in SPAMWT, so that the SPAMWT of rats in the control group (2) and PAH-induced dofetilide-treated group (4) were statistically similar (FIG. 6B).

Example 6

Lower Doses of Kv11.1 Channel Blocker Dofetilide Reverse Pulmonary Artery Wall Remodeling of PAH-Induced Rats To examine further if pharmacological inhibition of Kv11.1 channels would affect PAH progression, healthy and PAH-induced SD rats are treated with Kv11.1 channel-specific blocker dofetilide using lower doses (1 mg/kg, 0.1 mg/kg, 0.01 mg/kg, or 0.001 mg/kg) than was used in Example 5. Lung tissues from four groups of SD rats (four rats in each group) are examined with H&E staining. The rats in two control groups, Group (1) injected with DMSO and Group (2) injected with dofetilide, have similar lung structure and no statistical differences in small pulmonary arterial media wall thickness (SPAMWT). PAH-induced rats in Group (3) have increased intimal endothelial cell proliferation, increased SPAMWT, and reduced pulmonary arterial lumen diameter compared to control rats. Surprisingly, PAH-induced, dofetilide-treated rats in Group (4) have reduced SPAMWT and increased pulmonary arterial lumen diameter compared with PAH-induced rats in Group (3). Remarkably, dofetilide completely eliminates PAH-induced changes in SPAMWT, so that the SPAMWT of rats in the control Group (2) and PAH-induced dofetilide treated Group (4) are statistically similar.

The examples above show that Kv11.1 channels are expressed in the lungs of rats and humans. In healthy lung tissues Kv11.1 expression was limited to the SMC layer of bronchioles and large pulmonary arteries with diameters >100 μm. In rats with PAH and humans with COPD-associated pulmonary hypertension, Kv11.1 channel expression was detected not only in the large pulmonary arteries but also in the small pulmonary arteries with diameters <100 μm. Importantly, treatment with Kv11.1 channel blocker dofetilide prevented vascular remodeling in PAH-induced rats and maintained the small pulmonary arterial media wall thickness at the level seen in healthy rats. Dofetilide, also known as TIKOSYN®, is clinically used to treat atrial fibrillation. These results provide rationale for further exploring the modulation of Kv11.1 channels as a potential therapy in pulmonary hypertension treatment and repurposing TIKOSYN® for treatment of PAH and COPD patients.

Kv11.1 channels are abundantly expressed in the heart[31, 32] and brain[11, 32]. In the heart, Kv11.1 channels are expressed in cardiac myocytes[33, 34], and their function is to repolarize cardiac action potential[1-4]. In the brain, Kv11.1 channels are expressed in various regions, and their function is to regulate neuronal excitability[11, 35-37]. In addition to the heart and brain, Kv11.1 channels are also expressed in a variety of other tissues and organs[10], including retina[15], chromaffin cells[38], and SMCs of gallbladder[16], stomach[17] and intestines[18-20].

Although Kv11.1 channel mRNA has been reported in rat lung tissue[32], the Kv11.1 channel protein expression pattern has not been known. Histological examination of the human and rat lung tissue disclosed herein indicated that Kv11.1 channels are expressed in the SMC layer of large diameter pulmonary arteries (FIGS. 1C, 1D and 3C, left panel). Interestingly, in healthy lungs no Kv11.1 channel expression was detected in the SMC layer of the small diameter pulmonary arteries (FIGS. 1E, 1F and 3C, right panel). These findings indicate that Kv11.1 channels are part of the ion channel landscape of lung smooth muscles and should be considered a novel target for their modulation.

Acute hypoxia causes constriction of pulmonary arteries mediated by the changes in the SMCs with oxygen deprivation[39]. Interestingly, hypoxia-induced constriction of pulmonary arteries is observed only in the small diameter pulmonary arteries[40]. The mechanism of the different contractile response of the small and large diameter pulmonary arteries is not known. It has been proposed that distinct hypoxia-induced cellular signaling of the SMCs in the small and large diameter pulmonary arteries may be responsible for the difference in the contractile response in hypoxia[39, 41]. For instance, opposite changes in the intracellular calcium and pH were observed in the SMCs from small and large diameter arteries in response to hypoxia[42, 43]. Moreover, inherent differences were reported in the protein expression levels between the SMCs of the large and small diameter pulmonary arteries even in the absence of hypoxia[41]. It has been shown that telokin, a smooth muscle protein involved in the regulation of myosin phosphorylation, is strongly expressed in the small diameter arteries and only weakly expressed in the large diameter pulmonary arteries[41].

The finding disclosed herein that that Kv11.1 channels are present in SMCs of large but not small pulmonary arteries in normal lungs further supports the hypothesis of the inherent differences in the properties of SMCs from small and large pulmonary arteries. The appearance of Kv11.1 channels in small pulmonary arteries of PAH rats and humans with COPD-associated pulmonary hypertension (FIGS. 2B and 4C) suggests that the Kv11.1 channel expression is linked to vasculature remodeling in hypoxia. This is further supported by the time course of changes in Kv11.1 channel expression. The Kv11.1 channel expression increased gradually in the PAH-induced rats with the time course closely following the arterial wall thickening (FIG. 5).

To test if pharmacological inhibition of Kv11.1 channels could affect the vascular remodeling in PAH, the Kv11.1 channel blocker dofetilide was injected at the time of PAH-induction. Surprisingly, dofetilide substantially reduced the PAH-associated vascular remodeling in the dofetilide-treated rats (FIG. 6). Dofetilide increased the lumen diameter and decreased the pulmonary artery wall thickness to levels seen in control rats without PAH. This finding suggests that inhibition of Kv11.1 channels has a protective effect in pulmonary hypertension.

The effect of dofetilide is opposite to what would be expected based on a traditional role of $K^+$ channels as hyperpolarization generators in SMCs. Kv11.1 channels have been shown to regulate excitability of SMCs in various tissues, including epididymal duct[44], gastrointestinal tract[16, 18, 45], gallbladder[14] and portal vein[46], by contributing to the resting membrane potential and to the repolarization phase of the action potential[34, 47, 48]. Based on these reports, Kv11.1 channels would be expected to hyperpolarize SMCs in lung tissue and decrease the SMCs contractile tone. Therefore, Kv11.1 channels would be expected to play a protective role in PAH and Kv11.1 channel blockers would then be expected to exacerbate PAH-induced vascular remodeling, which is opposite to what is disclosed herein.

The findings disclosed herein can be reconciled based on another well-established role of Kv11.1 channels. Kv11.1 channels are also known to regulate cell proliferation during normal development and cancer[49]. Kv11.1 channel-mediated hyperpolarization is thought to be critical for the progression of the normal cell cycle[50, 51]. Importantly, Kv11.1 channel expression is upregulated in many cancerous tissues[49, 52] and inhibition of Kv11.1 channel activity with Kv11.1 channel-specific blockers decreases cell proliferation[53]. Although the mechanism of Kv11.1 channel regulation of tumor progression is not completely clear, a few potential observations are worth mentioning. The promoter region of Kv11.1 channel gene contains binding sites for many oncoproteins, enabling Kv11.1 channels to regulate cell growth in response to the activation of oncogenes[54]. There is evidence of an interaction between Kv11.1 channels and β1 integrins that in turn affects cell migration[55]. The instant inventors hypothesize that similar to cancer, growth of SMCs in PAH is associated with overexpression of Kv11.1 channels, and application of Kv11.1 channel blocker dofetilide decreases SMC growth and PAH-associated vascular remodeling. It has been shown that nitric oxide (NO)[56] and $H_2O_2$[57], which are upregulated in hypoxia, block Kv11.1 channels. Therefore, the inhibition of Kv11.1 channels could be part of a protective cellular response in hypoxia-induced pulmonary hypertension aimed at decreasing the vascular remodeling.

Dofetilide, distributed under the trade name of TIKOSYN® by Pfizer, is an FDA approved drug used for the treatment of irregular heartbeat. As other Class III antiarrhythmic drugs, it acts by prolonging the cardiac action potential duration via blocking Kv11.1 channels in the heart[58]. Results of studies disclosed herein indicate that Kv11.1 channels are expressed in lungs and their inhibition by TIKOSYN® improves symptoms of arterial muscularization associated with PAH. Therefore, the findings disclosed herein warrant further investigation of the potentially positive effects of TIKOSYN® on patients with PAH. Notably, 0.4% of patients who take TIKOSYN® also have pulmonary hypertension[59]. For these patients the potentially positive effects of TIKOSYN® could be especially easily attainable with an optimized dosage of the drug.

Substantial differences in the gene expression and disease progression between human and animal models of pulmonary hypertension are well documented[60]. Animal strain-dependent differences are also frequent. For instance, fawn-hooded rat is known to develop more severe pulmonary hypertension-induced remodeling than other strains when exposed to hypoxia[61]. The findings disclosed herein that Kv11.1 channel expression in lungs, and pulmonary hypertension-associated changes in their expression, are conserved in both humans and Fisher/SD rats suggest the importance of Kv11.1 channel contribution to lung function and pulmonary hypertension progression.

In summary, the instant disclosure shows that in healthy humans and rats, Kv11.1 channels are expressed in SMCs of large pulmonary arteries only, while in humans with COPD-associated pulmonary hypertension and PAH-induced rats, Kv11.1 channels are expressed in both large and small pulmonary arteries. Inhibition of Kv11.1 channels by dofetilide decreased PAH-associated vascular remodeling, suggesting that Kv11.1 channel blockers might hold potential for the treatment of PAH.

REFERENCES

1. Schonherr R and Heinemann S H. Molecular determinants for activation and inactivation of HERG, a human inward rectifier potassium channel. *J. Physiol.* 1996; 493 (Pt 3):635-642.
2. Smith P L, Baukrowitz T and Yellen G. The inward rectification mechanism of the HERG cardiac potassium channel. *Nature.* 1996; 379:833-836.
3. Spector P S, Curran M E, Keating M T and Sanguinetti M C. Class III antiarrhythmic drugs block HERG, a human cardiac delayed rectifier K+ channel. Open-channel block by methanesulfonanilides. *Circ Res.* 1996; 78:499-503.
4. Trudeau M C, Warmke J W, Ganetzky B and Robertson G A. HERG, a human inward rectifier in the voltage-gated potassium channel family. *Science.* 1995; 269:92-95.
5. Curran M E, Splawski I, Timothy K W, Vincent G M, Green E D and Keating M T. A molecular basis for cardiac arrhythmia: HERG mutations cause long QT syndrome. *Cell.* 1995; 80:795-803.
6. Kiehn J, Lacerda A E, Wible B and Brown A M. Molecular physiology and pharmacology of HERG. Single-channel currents and block by dofetilide. *Circulation.* 1996; 94:2572-2579.
7. Sanguinetti M C, Jurkiewicz N K, Scott A and Siegl P K. Isoproterenol antagonizes prolongation of refractory period by the class III antiarrhythmic agent E-4031 in guinea pig myocytes. Mechanism of action. *Circ Res.* 1991; 68:77-84.
8. Zhou Z, Gong Q, Epstein M L and January C T. HERG channel dysfunction in human long QT syndrome. Intracellular transport and functional defects. *J. Biol Chem.* 1998; 273:21061-21066.
9. Bianchi L, Wible B, Arcangeli A, Taglialatela M, Morra F, Castaldo P, Crociani O, Rosati B, Faravelli L, Olivotto M and Wanke E. herg encodes a K+ current highly conserved in tumors of different histogenesis: a selective advantage for cancer cells? *Cancer Res.* 1998; 58:815-22.
10. Babcock J J and Li M. hERG channel function: beyond long QT. *Acta Pharmacol Sin.* 2013; 34:329-35.
11. Guasti L, Cilia E, Crociani O, Hofmann G, Polvani S, Becchetti A, Wanke E, Tempia F and Arcangeli A. Expression pattern of the ether-a-go-go-related (ERG) family proteins in the adult mouse central nervous system: evidence for coassembly of different subunits. *J Comp Neurol.* 2005; 491:157-74.
12. Papa M, Boscia F, Canitano A, Castaldo P, Sellitti S, Annunziato L and Taglialatela M. Expression pattern of the ether-a-gogo-related (ERG) K+ channel-encoding genes ERG1, ERG2, and ERG3 in the adult rat central nervous system. *J Comp Neurol.* 2003; 466:119-35.
13. Cordeiro S, Guseva D, Wulfsen I and Bauer C K. Expression pattern of Kv11 (Ether a-go-go-related gene; erg) K+ channels in the mouse retina. *PLoS One.* 2011; 6:e29490.
14. Parr E, Pozo M J, Horowitz B, Nelson M T and Mawe G M. ERG K+ channels modulate the electrical and contractile activities of gallbladder smooth muscle. *Am J Physiol Gastrointest Liver Physiol.* 2003; 284:G392-8.
15. Ohya S, Asakura K, Muraki K, Watanabe M and Imaizumi Y. Molecular and functional characterization of ERG, KCNQ, and KCNE subtypes in rat stomach smooth muscle. *Am J Physiol Gastrointest Liver Physiol.* 2002; 282:G277-87.
16. Farrelly A M, Ro S, Callaghan B P, Khoyi M A, Fleming N, Horowitz B, Sanders K M and Keef K D. Expression and function of KCNH2 (HERG) in the human jejunum. *Am J Physiol Gastrointest Liver Physiol.* 2003; 284:G883-95.
17. Lamarca V, Grasa L, Fagundes D S, Arruebo M P, Plaza M A and Murillo M D. K+ channels involved in contractility of rabbit small intestine. *J Physiol Biochem.* 2006; 62:227-36.
18. Lillich J D, Rakestraw P C, Roussel A J, Finley M R, Ganta S and Freeman L C. Expression of the ether-a-go-go (ERG) potassium channel in smooth muscle of the equine gastrointestinal tract and influence on activity of jejunal smooth muscle. *Am J Vet Res.* 2003; 64:267-72.
19. Bartoszewski R, Matalon S and Collawn J F. Ion channels of the lung and their role in disease pathogenesis. *Am J Physiol Lung Cell Mol Physiol.* 2017; 313:L859-L872.
20. Shujaat A, Minkin R and Eden E. Pulmonary hypertension and chronic cor pulmonale in COPD. *Int J Chron Obstruct Pulmon Dis.* 2007; 2:273-82.
21. Boucherat O, Chabot S, Antigny F, Perros F, Provencher S and Bonnet S. Potassium channels in pulmonary arterial hypertension. *Eur Respir J.* 2015; 46:1167-77.
22. Austin E D and Loyd J E. The genetics of pulmonary arterial hypertension. *Circ Res.* 2014; 115:189-202.
23. Dodson M W, Brown L M and Elliott C G. Pulmonary Arterial Hypertension. *Heart Fail Clin.* 2018; 14:255-269.
24. Farber H W and Loscalzo J. Pulmonary arterial hypertension. *N Engl J Med.* 2004; 351:1655-65.
25. Higenbottam T. Pulmonary hypertension and chronic obstructive pulmonary disease: a case for treatment. *Proc Am Thorac Soc.* 2005; 2:12-9.
26. Weir E K and Olschewski A. Role of ion channels in acute and chronic responses of the pulmonary vasculature to hypoxia. *Cardiovasc Res.* 2006; 71:630-41.
27. Dunham-Snary K J, Wu D, Sykes E A, Thakrar A, Parlow L R G, Mewburn J D, Parlow J L and Archer S L. Hypoxic Pulmonary Vasoconstriction: From Molecular Mechanisms to Medicine. *Chest.* 2017; 151:181-192.
28. Ibrahim Y F, Shults N V, Rybka V and Suzuki Y J. Docetaxel Reverses Pulmonary Vascular Remodeling by Decreasing Autophagy and Resolves Right Ventricular Fibrosis. *J Pharmacol Exp Ther.* 2017; 363:20-34.
29. Ibrahim Y F, Wong C M, Pavlickova L, Liu L, Trasar L, Bansal G and Suzuki Y J. Mechanism of the susceptibility of remodeled pulmonary vessels to drug-induced cell killing. *J Am Heart Assoc.* 2014; 3:e000520.
30. Oka M, Homma N, Taraseviciene-Stewart L, Morris K G, Kraskauskas D, Burns N, Voelkel N F and McMurtry I F. Rho kinase-mediated vasoconstriction is important in severe occlusive pulmonary arterial hypertension in rats. *Circ Res.* 2007; 100:923-9.
31. Shi W, Wymore R, Yu H, Wu J, Wymore R T, Pan Z, Robinson R B, Dixon J E, McKinnon D and Cohen I S.

Distribution and prevalence of hyperpolarization-activated cation channel (HCN) mRNA expression in cardiac tissues. *Circ Res.* 1999; 85:e1-e6.

32. Wymore R S, Gintant G A, Wymore R T, Dixon J E, McKinnon D and Cohen I S. Tissue and species distribution of mRNA for the IKr-like K+ channel, erg. *Circ Res.* 1997; 80:261-8.

33. Melnyk P, Ehrlich J R, Pourrier M, Villeneuve L, Cha T J and Nattel S. Comparison of ion channel distribution and expression in cardiomyocytes of canine pulmonary veins versus left atrium. *Cardiovasc Res.* 2005; 65:104-16.

34. Sanguinetti M C, Jiang C, Curran M E and Keating M T. A mechanistic link between an inherited and an acquired cardiac arrhythmia: HERG encodes the IKr potassium channel. *Cell.* 1995; 81:299-307.

35. Titus S A, Warmke J W and Ganetzky B. The Drosophila erg K+ channel polypeptide is encoded by the seizure locus. *J Neurosci.* 1997; 17:875-81.

36. Sacco T, Bruno A, Wanke E and Tempia F. Functional roles of an ERG current isolated in cerebellar Purkinje neurons. *J Neurophysiol.* 2003; 90:1817-28.

37. Furlan F, Taccola G, Grandolfo M, Guasti L, Arcangeli A, Nistri A and Ballerini L. ERG conductance expression modulates the excitability of ventral horn GABAergic interneurons that control rhythmic oscillations in the developing mouse spinal cord. *J Neurosci.* 2007; 27:919-28.

38. Gullo F, Ales E, Rosati B, Lecchi M, Masi A, Guasti L, Cano-Abad M F, Arcangeli A, Lopez M G and Wanke E. ERG K+ channel blockade enhances firing and epinephrine secretion in rat chromaffin cells: the missing link to LQT2-related sudden death? *FASEB J.* 2003; 17:330-2.

39. Madden J A, Vadula M S and Kurup V P. Effects of hypoxia and other vasoactive agents on pulmonary and cerebral artery smooth muscle cells. *Am J Physiol.* 1992; 263:L384-93.

40. Madden J A, Dawson C A and Harder D R. Hypoxia-induced activation in small isolated pulmonary arteries from the cat. *J Appl Physiol* (1985). 1985; 59:113-8.

41. Madden J A, Dantuma M W, Sorokina E A, Weihrauch D and Kleinman J G. Telokin expression and the effect of hypoxia on its phosphorylation status in smooth muscle cells from small and large pulmonary arteries. *Am J Physiol Lung Cell Mol Physiol.* 2008; 294:L1166-73.

42. Madden J A, Ray D E, Keller P A and Kleinman J G. Ion exchange activity in pulmonary artery smooth muscle cells: the response to hypoxia. *Am J Physiol Lung Cell Mol Physiol.* 2001; 280:L264-71.

43. Vadula M S, Kleinman J G and Madden J A. Effect of hypoxia and norepinephrine on cytoplasmic free Ca2+ in pulmonary and cerebral arterial myocytes. *Am J Physiol.* 1993; 265:L591-7.

44. Mewe M, Wulfsen I, Schuster A M, Middendorff R, Glassmeier G, Schwarz J R and Bauer C K. Erg K+ channels modulate contractile activity in the bovine epididymal duct. *Am J Physiol Regul Integr Comp Physiol.* 2008; 294:R895-904.

45. Akbarali H I, Thatte H, He X D, Giles W R and Goyal R K. Role of HERG-like K(+) currents in opossum esophageal circular smooth muscle. *Am J Physiol.* 1999; 277:C1284-90.

46. Ohya S, Horowitz B and Greenwood I A. Functional and molecular identification of ERG channels in murine portal vein myocytes. *Am J Physiol Cell Physiol.* 2002; 283:C866-77.

47. Zhu Y, Golden C M, Ye J, Wang X Y, Akbarali H I and Huizinga J D. ERG K+ currents regulate pacemaker activity in ICC. *Am J Physiol Gastrointest Liver Physiol.* 2003; 285:G1249-58.

48. Mewe M, Bauer C K, Schwarz J R and Middendorff R. Mechanisms regulating spontaneous contractions in the bovine epididymal duct. *Biol Reprod.* 2006; 75:651-9.

49. Vandenberg J I, Perry M D, Perrin M J, Mann S A, Ke Y and Hill A P. hERG K(+) channels: structure, function, and clinical significance. *Physiol Rev.* 2012; 92:1393-1478.

50. Arcangeli A, Bianchi L, Becchetti A, Faravelli L, Coronnello M, Mini E, Olivotto M and Wanke E. A novel inward-rectifying K+ current with a cell-cycle dependence governs the resting potential of mammalian neuroblastoma cells. *J Physiol.* 1995; 489 (Pt 2):455-71.

51. Crociani O, Guasti L, Balzi M, Becchetti A, Wanke E, Olivotto M, Wymore R S and Arcangeli A. Cell cycle-dependent expression of HERG1 and HERG1B isoforms in tumor cells. *J Biol Chem.* 2003; 278:2947-55.

52. Jehle J, Schweizer P A, Katus H A and Thomas D. Novel roles for hERG K(+) channels in cell proliferation and apoptosis. *Cell Death Dis.* 2011; 2:e193.

53. Smith G A, Tsui H W, Newell E W, Jiang X, Zhu X P, Tsui F W and Schlichter L C. Functional up-regulation of HERG K+ channels in neoplastic hematopoietic cells. *J Biol Chem.* 2002; 277:18528-34.

54. Lin H, Xiao J, Luo X, Wang H, Gao H, Yang B and Wang Z. Overexpression HERG K(+) channel gene mediates cell-growth signals on activation of oncoproteins SP1 and NF-kappaB and inactivation of tumor suppressor Nkx3.1. *J Cell Physiol.* 2007; 212:137-47.

55. Cherubini A, Hofmann G, Pillozzi S, Guasti L, Crociani O, Cilia E, Di Stefano P, Degani S, Balzi M, Olivotto M, Wanke E, Becchetti A, Defilippi P, Wymore R and Arcangeli A. Human ether-a-go-go-related gene 1 channels are physically linked to beta 1 integrins and modulate adhesion-dependent signaling. *Mol Biol Cell.* 2005; 16:2972-83.

56. Tagliatatela M, Pannaccione A, Iossa S, Castaldo P and Annunziato L. Modulation of the K(+) channels encoded by the human ether-a-gogo-related gene-1 (hERG1) by nitric oxide. *Mol Pharmacol.* 1999; 56:1298-308.

57. Kolbe K, Schonherr R, Gessner G, Sahoo N, Hoshi T and Heinemann S H. Cysteine 723 in the C-linker segment confers oxidative inhibition of hERG1 potassium channels. *J Physiol.* 2010; 588:2999-3009.

58. Ficker E, Jarolimek W, Kiehn J, Baumann A and Brown A M. Molecular determinants of dofetilide block of HERG K+ channels. *Circ Res.* 1998; 82:386-95.

59. eHealthMe. TIKOSYN and Pulmonary hypertension—from FDA reports eHealthMe. 2018; https://www.e-healthme.com/ds/tikosyn/pulmonary-hypertension/.

60. Colvin K L and Yeager M E. Animal Models of Pulmonary Hypertension: Matching Disease Mechanisms to Etiology of the Human Disease. *J Pulm Respir Med.* 2014; 4.

61. Sato K, Webb S, Tucker A, Rabinovitch M, O'Brien R F, McMurtry I F and Stelzner T J. Factors influencing the idiopathic development of pulmonary hypertension in the fawn hooded rat. *Am Rev Respir Dis.* 1992; 145:793-7.

The invention claimed is:

1. A method of treating pulmonary artery hypertension, comprising administering to a subject in need thereof an effective amount of a Kv11.1 channel inhibitor, wherein the Kv11.1 inhibitor is selected from the group consisting of dofetilide, haloperidol, terfenadine, astemizole, cisapride, and amiodarone.

2. The method of claim 1, wherein the pulmonary artery hypertension is not associated with chronic obstructive pulmonary disease (COPD).

3. The method of claim 1, wherein the pulmonary artery hypertension is associated with chronic obstructive pulmonary disease (COPD).

4. The method of claim 1, wherein the subject is not in need of treatment for irregular heart rhythm.

5. The method of claim 4, wherein the subject is not in need of treatment for atrial fibrillation.

6. The method of claim 1, wherein the subject is a human.

7. The method of claim 1, wherein the Kv11.1 inhibitor is dofetilide.

8. The method of claim 1, wherein the Kv11.1 inhibitor is administered orally.

9. The method of claim 1, wherein the Kv11.1 inhibitor is administered parenterally.

10. The method of claim 9, wherein the Kv11.1 inhibitor is administered intravenously or intraperitoneally.

11. The method of claim 1, wherein the Kv11.1 inhibitor is administered directly to lungs.

12. The method of claim 11, wherein the Kv11.1 inhibitor is administered intratracheally or by inhalation.

* * * * *

UNITED STATES PATENT AND TRADEMARK OFFICE
CERTIFICATE OF CORRECTION

PATENT NO. : 11,529,324 B2
APPLICATION NO. : 16/880376
DATED : December 20, 2022
INVENTOR(S) : Brelidze et al.

Page 1 of 1

It is certified that error appears in the above-identified patent and that said Letters Patent is hereby corrected as shown below:

In the Specification

At Column 1, Line 11:
Delete:
"STATEMENT OF GOVERNMENT SUPPORT
This invention was made with government support under
GM124020, HL072844 awarded by the National Institutes of Health. The government has certain rights in the invention."

And insert:
--STATEMENT OF GOVERNMENT SUPPORT
This invention was made with government support under grant numbers GM124020, HL072844 awarded by the National Institutes of Health. The government has certain rights in the invention.--

Signed and Sealed this
Second Day of September, 2025

Coke Morgan Stewart
*Acting Director of the United States Patent and Trademark Office*